United States Patent
Diner

(10) Patent No.: US 9,238,792 B2
(45) Date of Patent: Jan. 19, 2016

(54) COMPARTMENTALIZED SIMULTANEOUS SACCHARIFICATION AND FERMENTATION OF BIOMASS

(75) Inventor: Bruce A. Diner, Chadds Ford, PA (US)

(73) Assignee: E I DU PONT DE NEMOURS AND COMPANY, Wilmington, DE (US)

(*) Notice: Subject to any disclaimer, the term of this patent is extended or adjusted under 35 U.S.C. 154(b) by 794 days.

(21) Appl. No.: 12/871,976

(22) Filed: Aug. 31, 2010

(65) Prior Publication Data

US 2011/0212495 A1  Sep. 1, 2011

Related U.S. Application Data

(60) Provisional application No. 61/242,493, filed on Sep. 15, 2009.

(51) Int. Cl.
| | |
|---|---|
| *C12N 1/22* | (2006.01) |
| *C12M 1/00* | (2006.01) |
| *C12P 7/10* | (2006.01) |
| C12P 19/14 | (2006.01) |

(52) U.S. Cl.
CPC .............. *C12N 1/22* (2013.01); *C12M 29/18* (2013.01); *C12M 45/09* (2013.01); *C12P 7/10* (2013.01); *C12M 29/16* (2013.01); *C12P 19/14* (2013.01); *C12Y 302/01004* (2013.01); *Y02E 50/16* (2013.01); *Y02E 50/17* (2013.01)

(58) Field of Classification Search
CPC ......... C12M 29/18; C12M 29/16; C12P 7/10; C12P 19/14; C12Y 302/01004
See application file for complete search history.

(56) References Cited

U.S. PATENT DOCUMENTS

| | | | |
|---|---|---|---|
| 4,220,721 A | | 9/1980 | Emert et al. |
| 5,508,183 A | * | 4/1996 | Scott et al. .................... 435/165 |
| 2002/0164731 A1 | | 11/2002 | Eroma et al. |
| 2006/0154352 A1 | | 7/2006 | Foody et al. |
| 2007/0113840 A1 | | 5/2007 | Koivikko et al. |
| 2007/0246406 A1 | * | 10/2007 | Dibel et al. .................. 210/96.2 |
| 2007/0259412 A1 | | 11/2007 | Belanger et al. |
| 2008/0138872 A1 | | 6/2008 | Smith et al. |
| 2008/0283469 A1 | | 11/2008 | Pollock |
| 2009/0053777 A1 | | 2/2009 | Hennessey et al. |
| 2009/0053800 A1 | | 2/2009 | Friend et al. |
| 2009/0117635 A1 | | 5/2009 | Bradley et al. |
| 2009/0118477 A1 | | 5/2009 | Hallberg et al. |
| 2009/0171129 A1 | | 7/2009 | Evanko et al. |
| 2009/0281305 A1 | * | 11/2009 | Shimada et al. ......... 536/123.13 |

(Continued)

FOREIGN PATENT DOCUMENTS

| | | | |
|---|---|---|---|
| CN | 10117336 A | 5/2008 | |
| CN | 101173306 A | 5/2008 | |
| WO | WO 2006/112316 | * 10/2006 | ............... C07H 3/04 |

OTHER PUBLICATIONS

Roble, Noel D. et al., L-Lactic acid production from raw cassava starch in a circulating loop bioreactor with cells immobilized in loofa (*Luffa cylindrica*), Biotechnology Letters, 2003, pp. 1093-1098, vol. 25, No. 13, Kluwer Academic Publishers.

(Continued)

*Primary Examiner* — Jonathan Hurst

(57) ABSTRACT

Methods and apparatus' are disclosed for the simultaneous saccharification and fermentation of biomass providing for the compartmentalization of the saccharification process and the fermentation process resulting in decreased enzymatic end-product inhibition.

12 Claims, 3 Drawing Sheets

(56) References Cited

U.S. PATENT DOCUMENTS

2010/0015660 A1    1/2010   Leukes et al.
2010/0075413 A1    3/2010   Zijlstra et al.

OTHER PUBLICATIONS

Takagi, M. et al., A Method for Production of Alcohol Directly from Cellulose Using Cellulase and Yeast, Process Bioconversion Symposium, 1977, pp. 551-571, IIT Delhi.

Wyman, Charles E. et al., Simultaneous Saccharification and Fermentation of Several Lignocellulosic Feedstocks to Fuel Ethanol, Biomass and Bioenergy, 1992, pp. 301-307, vol. 3, No. 5, Pergamon Press Ltd, Great Britain.

Klei, H. E. et al., Hollow-Fiber Enzyme Reactors in Cellulose Hydrolysis, Biotechnology and Bioengineering Symposium, 1981, pp. 593-601, No. 11, John Wiley & Sons, Inc.

Engasser, J. M. et al., Hollow Fiber Enzyme Reactors for Maltose and Starch Hydrolysis, Chemical Engineering Science, 1980, pp. 99-105, vol. 35, Pergamon Press Ltd, Great Britain.

Kitano, Hiromi et al., Hollow Fiber Enzyme Reactors, Trends in Biotechnology, 1984, pp. 5-7, vol. 2, No. 1, Elsevier Science Publishers B.V., Amsterdam.

Hollow Fibers Manufacture and Applications, Jeanette Scott, ed., Gas and Liquid Separations and Concentrations, 1981, pp. 264-297, Noyes Data Corporation, Park Ridge, NJ.

Synthetic Membranes, Maynard B. Chenoweth, ed., Membrane Systems, pp. 53-87, Sixteenth Michigan Molecular Institute Meeting, Aug. 19-22, 1984, Midland, Michigan.

Leeper, Stephen A., Sep. Purif. Technol., Membrane Separations in the Recovery of Biofuels and Biochemicals: An Update Review, 1992, pp. 99-194.

International Search Report dated Oct. 28, 2010, International Application No. PCT/US/1048851.

Supplementary European Search Report, dated Nov. 18, 2014, EP Application No. 10817728.

\* cited by examiner

COMPARTMENTALIZED SIMULTANEOUS SACCHARIFICATION AND FERMENTATION OF BIOMASS

FIELD OF THE INVENTION

This disclosure relates to the field of biomass saccharification and fermentation of the produced sugars. Specifically, methods and apparatus' are disclosed for the simultaneous saccharification and fermentation of biomass providing for the compartmentalization of the saccharification process and the fermentation process resulting in decreased enzymatic end-product inhibition.

BACKGROUND OF THE INVENTION

Biomass (cellulosic and lignocellulosic) feedstocks and wastes, such as agricultural residues, wood, forestry wastes, sludge from paper manufacture, and municipal and industrial solid wastes, provide a potentially large renewable feedstock for the production of chemicals, plastics, fuels and feeds. Cellulosic and lignocellulosic feedstocks and wastes, composed of carbohydrate polymers comprising cellulose, hemicellulose and pectins, are generally treated by a variety of chemical, mechanical and enzymatic (enzymatic saccharification) means to release primarily hexose and pentose sugars, which can then be converted by microorganisms to useful products.

Enzymatic saccharification of biomass results in accumulation of cellobiose and glucose in the saccharification vessel producing end-product inhibition of exocellulases, slowing the rate of cellulose hydrolysis. Also produced is xylobiose which produces feedback inhibition of xylanases, slowing the rate of hemicellulose hydrolysis. The slowing of the rate of glucan and xylan hydrolysis may be partially relieved by the addition of higher concentrations of enzyme, however, this solution increases the cost of the process.

Previous methods to address the end-product inhibition during enzymatic saccharification include: use of simultaneous saccharification and fermentation (SSF; Takagi, M., et al., In: Process Bioconversion Symposium, 551-571, 1977) wherein the two steps of saccharification and fermentation were combined.

Combining the two process steps in SSF during biofuel production has a lower capital cost and the presence of the biofuel product lowers the risk of fermentation contamination (Wyman, C. E., et al., Biomass Bioenergy, 3: 301-307, 1992). In addition, in this method the formed glucose is consumed by the fermenting microorganism, relieving the end-product inhibition of both β-glucosidase and cellobiohydrolase enzymes. Formation of cellobiose from cellulose as well as its hydrolysis to glucose is thereby accelerated, increasing the rate of conversion of cellulose to glucose. Another approach to relieving glucose end-product inhibition was described in (WO 2006/101832) wherein the reversible conversion of glucose to fructose and xylose to xylulose partially relieved the end-product inhibition.

Klei et al., (Biotechnol. Bioeng. Symp. (1981) 11 Symp. Biotechnol. Energy Prod. Conserve., $3^{rd}$, 593-601) discussed use of immobilized β-glucosidase from *Aspergillus phoenicis* in hollow fiber ultrafiltration membrane cartridges, used as enzyme reactors, whereby hydrolysis of cellobiose occurred. This system was also used for circulation of cellulases from *Trichoderma reesei* during saccharification of cellulose. Application of hollow fiber membranes allows continuous processing of cellulose and significantly reduces cellulase requirements.

In U.S. Pat. No. 4,220,721, simultaneous saccharification and fermentation was performed by reusable endoglucanase and cellobiohydrolase enzymes adsorbed to a solid support.

CN101173306 describes combined enzymatic hydrolysis and continuous fermentation for acetone and butanol manufacturing from steam-exploded straw in a hollow fiber membrane reactor. It was indicated that the cellulase enzyme used for enzymatic hydrolysis of the straw could be recycled using the membrane reactor for high efficiency and low cost.

Methods described above have each partially improved the saccharification process and minimally relieved the end-product inhibition during saccharification.

The methods disclosed in the art notwithstanding, more efficient methods are needed to address the problem of end-product inhibition of enzymatic saccharification during simultaneous saccharification and fermentation.

SUMMARY OF THE DISCLOSURE

The present disclosure solves the stated problem above by providing methods and apparatus for compartmentalized simultaneous saccharification and fermentation of pretreated biomass using a hollow fiber circulation loop in which certain oligosaccharide hydrolyzing enzymes are sequestered. The methods and apparatus provide for removal of biomass components that may cause feedback inhibition of saccharification enzymes during saccharification of pretreated biomass to improve release of fermentable sugars during saccharification and increase target product yields by virtue of increased saccharification efficiency.

One aspect of the invention is directed to an apparatus for processing pretreated biomass comprising: a saccharification vessel and a separate fermentation vessel wherein said vessels are connected by two external circulation loops and a hollow fiber circulation loop that connects the two external circulation loops and comprises semi-permeable membranes wherein said apparatus provides for compartmentalized simultaneous saccharification and fermentation of pretreated biomass.

In another aspect, an apparatus is provided in accordance with FIG. 2, wherein said apparatus comprises a saccharification vessel (1) that is connected to a first external circulation loop (2) and wherein said first external circulation loop (2) is external to and connected to a first semi-permeable membrane (10) of a hollow fiber circulation loop (3); and said hollow fiber circulation loop (3) is connected to a second external circulation loop (4) that is external to and connected to a second semi-permeable membrane (11) of the hollow fiber circulation loop (3); and said second external circulation loop (4) is connected to a fermentation vessel (5) with an outlet for a target product (6). This apparatus may further comprise a series of circulation pumps including a first circulation pump (7) for the first external circulation loop (2); a second circulation pump (8) for the second external circulation loop (4); a third circulation pump (9) for the internal hollow fiber loop (3).

In another aspect a method of processing pretreated biomass is provided, said method comprising:
(a) providing the apparatus of the invention as described in FIG. 2,
(b) providing a mixture of pretreated bulk biomass and a saccharification enzyme consortium to the saccharification vessel (1) of said apparatus wherein said mixture produces by saccharification both high and low molecular weight components;
(c) providing at least one sequestered enzyme in the hollow fiber circulation loop (3);

(d) delivering an amount of the mixture of (b) through the first circulation loop over a first hollow fiber semi-permeable membrane (10) whereby said high molecular weight components of the mixture of (b) do not diffuse through said membrane and said low molecular weight components of the mixture diffuse through said membrane into the hollow fiber circulation loop (3);

(e) hydrolyzing the low molecular weight components that diffuse into the hollow fiber circulation loop (3) in (d) by said at least one sequestered enzyme in said hollow fiber circulation loop whereby hydrolysate comprising fermentable sugars is formed; and (f) delivering hydrolysate comprising fermentable sugars through a second semi-permeable membrane (11) into a second circulation loop (4) and to a fermentation vessel (5);

wherein pretreated biomass components are circulated throughout the apparatus by circulation pumps. In another aspect, the fermentable sugars of (e) delivered to the fermentation vessel of (f) are converted by at least one microorganism to at least one target product.

In another aspect of the above method, the presence of the first and second semi-permeable membranes prevents loss of one or more sequestered enzyme by preventing its diffusion into said saccharification and fermentation vessels.

In another aspect of the above method, the hydrolysate formed by the action of said sequestered enzyme on biomass is delivered to said fermentation vessel to relieve end-product feedback inhibition in the saccharification vessel.

In another aspect of the above method the molecular weight permeability of said first and second semi-permeable membranes is from about 10 to about 30 kilo-Daltons.

In another aspect of the invention, a method for compartmentalized simultaneous saccharification and fermentation of pretreated biomass is provided, said method comprising (a) providing pretreated biomass and a saccharification enzyme consortium to a saccharification vessel whereby saccharification products are formed and moved through one or more semi-permeable membranes passing through at least one compartment comprising one or more additional sequestered enzymes whereby hydrolysate comprising fermentable sugars is formed; and (b) delivering said hydrolysate to a separate fermentation vessel for fermentation to a target product.

BRIEF DESCRIPTION OF THE FIGURES

FIG. 1A depicts the saccharification time course from 0-120 h expressed as the percent of theoretical yield of monomeric glucose from acid/base pretreated sugar cane bagasse at different ratios of saccharification enzymes. The saccharification was performed in the presence of 50 mM NaCitrate, pH 4.6, 1%) Tween 20 (w/v) and 0.01% $NaN_3$ (w/v) at a solids loading of 11%. The enzyme ratios (mg protein/g cellulose) were: 4:3:8, 8:3:4, 6:3:6, 6:6:12, 12:6:1.2 and 12:6:12 for Spezyme® CP cellulase, Multifect® xylanase, and Novozyme 188 enzymes, respectively. FIG. 1B depicts a comparison of the monomeric glucose yields at 120 h from FIG. 1A for the different enzyme ratios.

DETAILED DESCRIPTION OF THE INVENTION

Figure 1A:
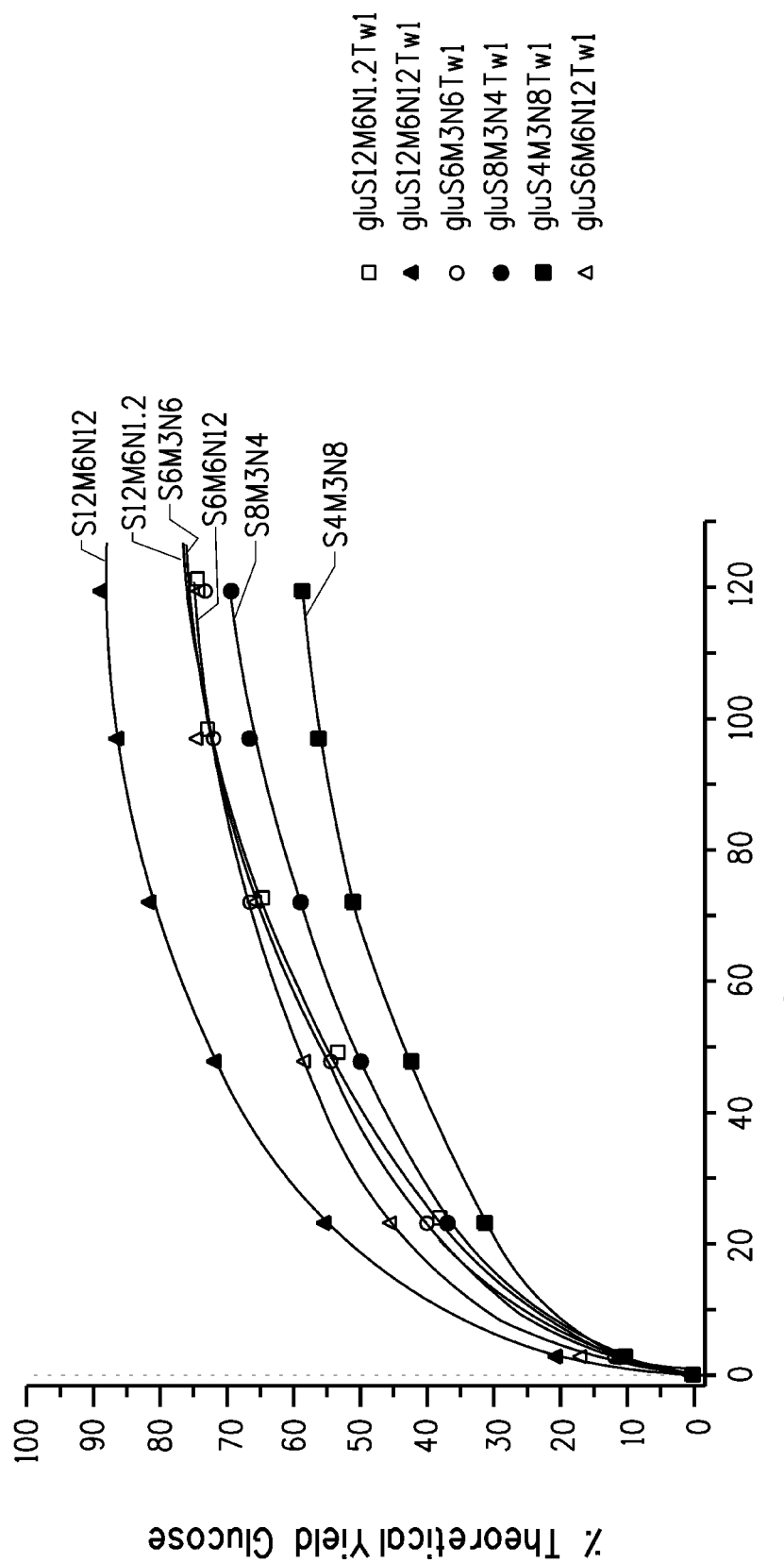
FIGS. 1A and 1B.

Applicants specifically incorporate the entire content of all cited references in this disclosure. Unless stated otherwise, all percentages, parts, ratios, etc., are by weight. Trademarks are shown in upper case. Further, when an amount, concentration, or other value or parameter is given as either a range, preferred range or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

The present apparatus and methods provide for relief of end-product inhibition of enzymatic saccharification during compartmentalized simultaneous saccharification and fermentation (CSSF) by using hollow fiber semi-permeable membranes and a hollow fiber circulation loop to connect separate saccharification and fermentation vessels.

DEFINITIONS

For clarity, terms used herein are to be understood as described herein or as such term would be understood by one of ordinary skill in the art of the invention. Additional explanation of certain terms used herein, are provided below:

"Glucose" is a monosaccharide containing six carbon atoms with a chemical formula $C_6H_{12}O_6$ with an aldehyde (hemiacetal) functional group at C1.

"Glucan" refers to a polysaccharide of β-1,4-linked D-glucose monomers linked by glycosidic bonds.

"Arabinose" is a monosaccharide containing five carbon atoms, including an aldehyde functional group.

"Xylose" is a monosaccharide containing five carbon atoms with a chemical formula $C_5H_{10}O_5$ with an aldehyde (hemiacetal) functional group at C1.

"Cellobiose" is a disaccharide derived from condensation of two glucose molecules linked in a β(1,4) glycosidic linkage.

"Cellobiohydrolase" refers to enzymes that cleave cellobiose units from cellulose at the reducing and non-reducing ends.

"Xylobiose" is a disaccharide of xylose monomers with a β-1,4 glycosidic linkage between them.

"β-Xylosidase" refers to a group of enzymes that cleaves xylose containing oligomers linked by β-glycosidic linkages (e.g., xylobiose).

"β-Xylobiosidase" is an enzyme that hydrolyzes xylobiose to xylose.

"Xylan" refers to a linear polysaccharide comprised mainly of β-1,4-linked D-xylose units, which may contain branches with other sugars such as L-arabinose and D-xylose.

"Xylanase" refers to an enzyme which degrades the linear poly- and oligosaccharide β-1,4-xylan into xylose and xylose oligomers. Some xylanases will act upon branched chain oligomers of xylose.

"β-Glucosidase" is an enzyme that acts upon β1->4 bonds linking two glucose or glucose-substituted molecules (i.e., the disaccharide cellobiose). It catalyzes the hydrolysis of terminal non-reducing residues in β-D-glucosides with release of glucose.

"Arabinofuranosidase" refers to an enzyme that hydrolyzes the terminal non-reducing α-L-arabinofuranoside residues in arabinose-containing xylans.

"Exocellulases" refers to enzymes that release cellobiose from the reducing and non-reducing ends of cellulose, "Branched chain xylose oligomers" refers to an oligoxylose backbone on which are located branches of arabinose and xylose.

"Branched chain xylose oligomer hydrolyzing enzymes" refers to xylanases that hydrolyze branched chain xylose oligomers.

"Semi-permeable membrane" and "semi-permeable membrane filter" are used interchangeably herein and refer to a membrane that serves as a physical barrier that permits the passage of materials only up to a certain size, shape or character. Examples of semi-permeable membranes useful in this method include membranes made of one or more of polysulfone, hydroxylated polysulfone, polyethersulfone, hydroxylated polyethersulfone, sulfonated polysulfone, polyetherketone, polyetheretherketone, polyimide, and polyetherimide, . . . .

"Hollow fiber semi-permeable membrane" and "hollow fiber semi-permeable membrane filter" are a type of semi-permeable membrane made from fibers that are hollow and semi-permeable. In a hollow fiber semi-permeable membrane there is a large surface to volume ratio.

"First semi-permeable membrane" refers to the hollow fiber semi-permeable membrane that allows passage of certain components resulting from saccharification of the biomass from the saccharification vessel to the hollow fiber circulation loop.

"Second semi-permeable membrane" refers to the hollow fiber semi-permeable membrane that allows passage of sugars produced by sequestered enzymes in the hollow fiber circulation loop to the second external circulation loop. Both the first and second hollow fiber semi-permeable membranes are made of similar materials such as those indicated above.

"Selective removal of target product" or "target product selectively removed" means removing the target product without removing any other components within the fermentation vessel.

"Compartmentalized simultaneous saccharification and fermentation (CSSF)", in this context, refers to a process wherein fermentation of one or more sugars and saccharification of pretreated biomass occur simultaneously in separate vessels coupled through at east one circulation loop.

"Fermentation" means converting chemical substrates (via either aerobic or anaerobic processes) to target products using microorganisms.

"Fermentation vessel" means any suitable vessel for use herein such that the vessel is suitable for fermentation of substrates to target products by microorganisms.

"Hydrolysate" refers to the product resulting from saccharification of biomass. The saccharification products in hydrolysate will vary with hydrolysis by different saccharifying enzymes and for different time periods. Effective saccharification produces a hydrolysate containing fermentable sugars.

"Fermentable sugars" refers to a sugar content primarily comprising monosaccharides (some disaccharides may still be present) that can be used as a carbon source by a microorganism in a fermentation process to produce target product(s).

"Circulation pump" refers to a pump that causes the liquid suspensions in the various circulation loops to circulate and move through an apparatus.

"Target product" refers to a chemical, fuel, or chemical building block produced by fermentation. Product is used in a broad sense and includes molecules such as proteins, including, for example, peptides, enzymes and antibodies. Also contemplated within the definition of target product are ethanol and butanol.

"Biomass" refers to any lignocellulosic material, including cellulosic and hemi-cellulosic material, for example, bioenergy crops, agricultural residues, municipal solid waste, industrial solid waste, yard waste, wood, forestry waste and combinations thereof, and as further described below. This biomass has a carbohydrate content that comprises polysaccharides and oligosaccharides and may also comprise additional components, such as lignin, protein and lipid.

"Pretreated biomass" is biomass that has been treated by any means that facilitates enzymatic saccharification.

"Saccharification" or "enzymatic saccharification" refers to production of fermentable sugars from polysaccharides by the action of hydrolytic enzymes. Production of fermentable sugars from pretreated biomass occurs by enzymatic saccharification by cellulolytic and hemicellulolytic enzymes.

"Saccharification vessel" means any vessel suitable for use herein for saccharification of biomass. The saccharification vessel may comprise pretreated biomass wherein enzymatic saccharification takes place.

"Enzyme consortium" or "saccharification enzyme consortium" is a collection of hydrolytic enzymes. These enzymes are typically secreted by a microorganism. The saccharification enzyme consortium will typically contain one or more cellulases, xylanases, glycosidases, and esterases. In the present invention, the saccharification enzyme consortium added to the saccharification vessel need not contain β-xylosidase, β-glucosidase and arabinofuranosidases as these are included in the hollow fiber circulation loop.

"Sequestered enzymes" as used herein refers to enzymes such as β-glucosidase, β-xylosidase, and arabinofuranosidases and xylanases, that are sequestered within the hollow fiber circulation loop and are capable of hydrolyzing glucose oligomers, and straight chain and branched chain xylose oligomers of biomass.

"End-product feedback inhibition" refers to a situation where accumulation of the product of an enzymatic reaction inhibits the reaction leading to its formation. In this disclosure, for example, exocellulases are feedback inhibited by cellobiose and to some extent by glucose and xylanases are feedback inhibited by xylobiose and to some extent by xylose. β-glucosidase is feedback inhibited by its product, glucose. β-Xylobiosidase is inhibited by its product xylose.

"Circulation loop" refers to a liquid circulation loop that circulates the contents of either the saccharification or the fermentation vessel over the outer surfaces of the first or second semi-permeable membranes adjacent to the hollow fiber circulation loop, respectively.

"First external circulation loop" is a fluid circulation loop that passes the biomass and the saccharification enzyme consortium from the saccharification vessel over the outer surface of the first semi-permeable membrane of the hollow fiber circulation loop.

"Second external circulation loop" is a fluid circulation loop that passes the contents of the fermentation vessel over the outer surface of the second semi-permeable membrane of the hollow fiber circulation loop picking up the glucose, xylose and arabinose that diffuse across the membrane and delivering them to the fermentation vessel.

"Hollow fiber circulation loop" refers to a fluid circulation loop that contains the first and second semi-permeable membrane filters and the one or more sequestered enzymes, where enzymatic hydrolysis occurs and products are transported between the saccharification and the fermentation vessels via the first and second external circulation loops, through the first and second semi-permeable membranes.

"Selective delivery of certain components" refers to delivery of certain size components (e.g., oligosaccharides such as cellobiose, xylobiose and branched chain xylose oligomers) of the saccharified biomass from the saccharification vessel through the first semi-permeable membrane filter to the hollow fiber circulation loop and through the second semi-permeable membrane filter to the fermentation vessel.

"High molecular weight components" refers to the components of biomass with molecular weights higher than 30 KD that cannot diffuse through the semi-permeable membrane filter of the hollow fiber loop.

"Low molecular weight components" refers to the components of biomass with molecular weights less than 30 KD that can diffuse through the semi-permeable membrane filter of the hollow fiber loop.

Biomass

Biomass suitable for the method described herein includes, but is not limited to, bioenergy crops, agricultural residues, municipal solid waste, industrial solid waste, sludge from paper manufacture, yard waste, wood and forestry waste. Examples of biomass include, but are not limited to corn cobs, crop residues such as corn husks, corn stover, grasses, wheat, wheat straw, barley, barley straw, hay, rice straw, switchgrass, waste paper, sugar cane bagasse, sorghum, soy, components obtained from milling of grains, trees, branches, roots, leaves, wood chips, sawdust, shrubs and bushes, vegetables, fruits, flowers and animal manure.

The biomass may be derived from a single source, or it can comprise a mixture derived from more than one source; for example, biomass could comprise a mixture of corn cobs and corn stover, or a mixture of stems or stalks and leaves.

In one embodiment, the biomass that is useful for the invention has a relatively high carbohydrate content, is relatively dense, and/or is relatively easy to collect, transport, store and/or handle. In another embodiment, the biomass may include agricultural residues such as corn stover, wheat straw, barley straw, oat straw, rice straw, canola straw, and soybean stover; grasses such as switch grass, miscanthus, cord grass, and reed canary grass; fiber process residues such as corn fiber, beet pulp, pulp mill fines and rejects and sugar cane bagasse; sorghum; forestry wastes such as aspen wood, other hardwoods, softwood and sawdust; and post-consumer waste paper products; as well as other crops or sufficiently abundant lignocellulosic material. In yet another embodiment, biomass that is useful comprises corn cobs, corn stover, sugar cane bagasse and switchgrass.

Pretreatment of Biomass Prior to Saccharification

In biomass, crystalline cellulose fibrils are embedded in a hemicellulose matrix which, in turn, is surrounded by an outer lignin layer. Pretreatment of the biomass is usually required to modify the lignin barrier for a more effective subsequent enzymatic saccharification process. Methods to pretreat biomass to prepare it for saccharification are well known in the art (e.g., Hsu, T.-A., 1996, *"Pretreatment of Biomass"*, in *Handbook on Bioethanol: Production and Utilization*, Wyman, C. E., ed., Taylor & Francis, Washington, D.C., 179-212; Ghosh, P., Singh, A., 1993 and U.S. Pat. No. 7,503,981, U.S. Pat. No. 7,504,245, U.S. Pat. No. 7,413,882, WO2008/112291). Some pretreatment methods are, for example, dilute acid hydrolysis (T. A. Lloyd and C. E Wyman, Bioresource Technol., 96: 1967, 2005), Ammonia Fiber Explosion (AFEX) technique (F. Teymouri et al., Bioresource Technol., 96: 2014, 2005), pH Controlled liquid hot water treatment (N. Mosier et al., Bioresource Technol., 96: 1986, 2005), aqueous ammonia recycle process (ARP) (T. H. Kim and Y. Y. Lee, Bioresource Technol., 96: 2007, 2005), lime pretreatment (S. Kim and M. T. Holzapple, Bioresource Technol., 96: 1994, 2005) and ionic liquid pretreatment (US 2008/0227162).

For biomass pretreatment the temperature, pH, time of pretreatment and concentration of reactants, concentration of one or more additional reagents, biomass concentration, biomass type and particle size are related; thus these variables may be adjusted as necessary for each type of biomass to optimize the pretreatment process.

The biomass of the current method may be pretreated by any of the methods described above. Alternatively, in one embodiment, to prepare the biomass of the present method for saccharification, it may be initially pretreated with 100 mM $H_2SO_4$ for 1 hour at 121° C. and washed with water.

In one embodiment, the biomass residue may be further suspended in 69% EtOH (v/v) containing 2.9% NaOH (w/v) and heated in a stainless steel pressure vessel (19 mL capacity) at 175° C. temperature for 140 minutes, cooled to room temperature, filtered and washed with 69% EtOH to remove undesirable breakdown products and lignin fragments. In another embodiment, the pretreated biomass may be air-dried. Drying may occur by conventional means, such as exposure at ambient temperature to vacuum or flowing air at atmospheric pressure, and/or heating in an oven or a vacuum oven.

The dried pretreated biomass may be then analyzed using analytical means well known in the art in order to determine the concentration of glucan, xylan and acid-insoluble lignin. The glucan and xylan contents of the dried pretreated biomass are used to determine the required enzyme loadings in the saccharification process.

Saccharification

Pretreated biomass may be hydrolyzed in the presence of a saccharification enzyme consortium to release oligosaccharides and/or monosaccharides in a hydrolysate. Surfactants such as Tween 20 or Tween 80 or polyoxyethylenes such as PEG 2000, 4000 or 8000 may be added to improve the saccharification process. Other surfactants such as those described in U.S. Pat. No. 7,354,743 B2, incorporated herein by reference, may also be used. Saccharification enzymes and methods for biomass treatment are reviewed in Lynd, L. R., et al. (Microbiol. Mol. Biol. Rev., 66: 506-577, 2002). The saccharification enzyme consortium may comprise one or more glycosidases; the glycosidases may be selected from the group consisting of cellulose-hydrolyzing glycosidases, hemicellulose-hydrolyzing glycosidases, and starch-hydrolyzing glycosidases. Other enzymes in the saccharification enzyme consortium may include peptidases, lipases, ligninases and acetyl and feruloyl esterases.

The saccharification enzyme consortium comprises one or more enzymes selected primarily, but not exclusively, from the group "glycosidases" which hydrolyze the glycosidic linkages of di-, oligo-, and polysaccharides and are found in the enzyme classification EC 3.2.1.x (Enzyme Nomenclature 1992, Academic Press, San Diego, Calif. with Supplement 1 (1993), Supplement 2 (1994), Supplement 3 (1995, Supplement 4 (1997) and Supplement 5 [in Eur. J. Biochem., 223: 1-5, 1994; Eur. J. Biochem., 232: 1-6, 1995; Eur. J. Biochem., 237: 1-5, 1996; Eur. J. Biochem., 250:1-6, 1997; and Eur. J. Biochem., 264:610-650, 1999, respectively]) of the general group "hydrolases" (EC 3.). Glycosidases useful in the present method can be categorized by the biomass component that they hydrolyze. Glycosidases useful for the present method include cellulose-hydrolyzing glycosidases (for example, cellulases, endoglucanases, exoglucanases, cellobiohydrolases, β-glucosidases), hemicellulose-hydrolyzing glycosidases (for example, xylanases, endoxylanases, exoxylanases, β-xylosidases, arabinofuranosidases, mannases, galactases, pectinases, glucuronidases), and starch-hydrolyzing glycosidases (for example, amylases, α-amylases, β-amylases, glucoamylases, α-glucosidases, isoamylases). Branched chain xylose oligomer hydrolyzing enzymes hydrolyze branched chain oligomers containing xylose and arabinose—e.g. L-α-arabinofuranosidase.

In addition, it may be useful to add other activities to the saccharification enzyme consortium such as peptidases (EC 3.4.x.y), lipases (EC 3.1.1.x and 3.1.4.x), ligninases (EC 1.11.1.x), and acetyl (EC 3.1.1.6) and feruloyl (EC 3.1.1.73) esterases to help release polysaccharides from other components of the biomass. It is well known in the art that microorganisms that produce polysaccharide-hydrolyzing enzymes often exhibit an activity, such as cellulose degradation, that is catalyzed by several enzymes or a group of enzymes having different substrate specificities. Thus, a "cellulase" from a microorganism may comprise a group of enzymes, all of which may contribute to the cellulose-hydrolyzing activity. Commercial or non-commercial enzyme preparations, such as cellulase, may comprise numerous enzymes depending on the purification scheme utilized to obtain the enzyme. Thus, the saccharification enzyme consortium of the present method may comprise enzyme activity, such as "cellulase", however it is recognized that this activity may be catalyzed by more than one enzyme.

As indicated above, in the present invention, the saccharification enzyme consortium added to the saccharification vessel need not contain β-xylosidase, β-glucosidase and arabinofuranosidases. One or more of these enzymes will be sequestered within the hollow fiber circulation loop. Xylanase enzymes, that act on both polymeric and oligomeric xyloses, may be included in the saccharification enzyme consortium in the saccharification vessel and may also be sequestered within the hollow fiber circulation loop.

Saccharification enzymes may be obtained commercially, in isolated form, such as Spezyme® CP cellulase (Genencor International, Rochester, N.Y.) and Multifect® Xylanase (Genencor). In addition, saccharification enzymes may be unpurified and provided as a type of cell extract or whole cell preparation. The enzymes may be produced using recombinant microorganisms that have been engineered to express multiple saccharifying enzymes. One skilled in the art would know how to determine the effective amount of enzymes to use in the consortium and adjust conditions for optimal enzyme activity. One skilled in the art would also know how to optimize the classes of enzyme activities required within the consortium to obtain optimal saccharification of a given pretreatment product under the selected conditions.

Preferably the saccharification reaction is performed at or near the temperature and the pH optima for the saccharification enzymes. The temperature optimum used with the saccharification enzyme consortium in the present method ranges from about 15° C. to about 100° C. In another embodiment, the temperature optimum ranges from about 20° C. to about 80° C. and most typically 45-50° C. The pH optimum can range from about 2 to about 11. In another embodiment, the pH optimum used with the saccharification enzyme consortium in the present method ranges from about 4 to about 5.5.

The saccharification may be performed for a time of about several minutes to about 120 hours, and preferably from about several minutes to about 48 hours. The time for the reaction will depend on enzyme concentration and specific activity, as well as the substrate used, its concentration (i.e. solids loading) and the environmental conditions, such as temperature and pH. One skilled in the art can readily determine optimal conditions of temperature, pH and time to be used with a particular substrate and saccharification enzyme(s) consortium.

The saccharification may be performed batch-wise or as a continuous process. The saccharification may also be performed in one step, or in a number of steps. For example, different enzymes required for saccharification may exhibit different pH or temperature optima. A primary treatment may be performed with enzyme(s) at one temperature and pH, followed by secondary or tertiary (or more) treatments with different enzyme(s) at different temperatures and/or pH. In addition, treatment with different enzymes in sequential steps may be at the same pH and/or temperature, or different pHs and temperatures, such as using hemicellulases stable and more active at higher pHs and temperatures followed by cellulases that are active at lower pHs and temperatures.

The degree of solubilization of sugars from biomass following saccharification may be monitored by measuring the release of monosaccharides and oligosaccharides. Methods to measure monosaccharides and oligosaccharides are well known in the art. For example, the concentration of reducing sugars can be determined using the 1,3-dinitrosalicylic (DNS) acid assay (Miller, G. L., Anal. Chem., 31: 426-428, 1959). Alternatively, sugars may be measured by HPLC using an appropriate column as described below.

Compartmentalizing SSF

In the present method, compartmentalized SSF (CSSF) was developed to remove feedback inhibition of some of the saccharification enzymes typically present in a saccharification enzyme consortium, during saccharification of the pretreated biomass. In some cases, the product feedback inhibition may be in part overcome by addition of more enzymes to the saccharification vessel thus diminishing the loss of enzyme activity due to feedback inhibition during saccharification. However, addition of more enzymes to the saccharification process, while speeding the hydrolytic reactions, is expensive and increases the total cost of the process. To eliminate the problem of feedback inhibition of the saccharification enzymes by their end-products, the end-products need to be constantly removed to avoid their accumulation.

In this instance, the saccharification enzymes' feedback inhibition is relieved through application of CSSF and sequestering some of the hydrolyzing enzymes in a separate compartment, such as a hollow fiber circulation loop. Diffusion of the enzymes' substrates from the saccharification vessel via a first semi-permeable membrane filter into a separate enzyme containing compartment lowers their concentration in the saccharification vessel thereby, removing the potential of feedback inhibition of saccharification enzyme consortium enzymes by their products. The sequestered enzymes (e.g., β-xylosidase, β-glucosidase, and arabinofuranosidase) in the enzyme containing compartment hydrolyze their substrates to the desired monosaccharide products. The products move through a second semi-permeable membrane, where they diffuse into the fermentation vessel. Both first and second semi-permeable membranes have a molecular weight cutoff of from 10 to about 30 kDa which would allow only passage of small molecules (i.e., soluble oligosaccharides including small branched chain xylose oligomers).The sequestered enzymes remain in the separate compartment since they are not able to pass through the first or second semi-permeable membranes. Hydrolysis of the disaccharides to their monosaccharides and their conversion to the target product reduces end-product inhibition of the enzymes in the saccharification vessel. Sequestering enzymes in a hollow fiber circulation loop allows their repeated use during saccharification, without the need for an enzyme recovery process. Having separate saccharification and fermentation vessels allows the vessels to be run at different temperatures and also prevents the fermenting cells from adhering to undigested biomass.

Hollow Fiber Semi-Permeable Membranes

In one embodiment the semi-permeable membrane is a hollow fiber semi-permeable membrane. Hollow fiber semi-permeable membranes offer unique benefits of high membrane packing densities, high surface/volume ratios, sanitary designs and, due to their structural integrity and construction, they can withstand permeate backpressure, thus allowing flexibility in system design and operation.

Hollow fiber semi-permeable membranes serve as physical barriers that permit the passage of materials only up to certain sizes, shapes or characters and are well known in the art (e.g., Hollow fiber manufacture and application, Chem. Technol, Rev., volume 194, Edited by J. Scott, 1981, Noyes Data Corp., Park Ridge, N.J. and Synthetic membranes, Edited by M. B. Chenweth, page 63, 1986, Harwood Academic Press, NY, NY and Leeper, S. A., Membrane separation in the recovery of biofuels and biochemiclas: an update review, Sep. Purif. Technol., pages 99-194, 1992). Two basic morphologies of hollow fiber semi-permeable membranes are "isotropic" and "anisotropic". Membrane separation is achieved by using these morphologies.

The "anisotropic" configuration contains a dense, semi-permeable, ultrathin skin that overlies a supporting porous structure. "Isotropic" microporous polysulfone semi-permeable membranes can be prepared by using a particular combination of casting solution and precipitation solution formulation, and casting conditions. Both hollow fiber and flat membranes can be prepared in this manner. The isotropic membranes are skinless and are characterized by uniform porosity throughout the membrane. For the purposes of the disclosed method herein, both types of hollow fiber semi-permeable membranes may be used.

Since in a hollow fiber filtration process no phase change is involved and no latent heat is needed, hollow fiber semi-permeable membrane systems have modest energy requirements. In addition, hollow fiber semi-permeable membranes have large membrane surface per module volume. Hence, while the size of a hollow fiber semi-permeable membrane may be smaller than other types of membranes it can give higher performance.

Hollow fiber semi-permeable membranes are flexible and they can perform filtration by either an "inside-out" or an "outside-in" process. Furthermore, hollow fiber semi-permeable membranes have low operating costs compared to other types of unit operations. Hollow fiber semi-permeable membrane bioreactors are known in the art (WO2007/004170 and WO2008/006494 and WO2007/120449 and US2002/0164731) and (Engasser, J. M., et al., Chem. Eng. Sci., 35: 99-105, 1980 and Kitano, H. and Ise, N., Treands in Biotechnol., 2: 5-7, 1984). Hollow fiber semi-permeable membrane bioreactors can be operated continuously and have the advantage of high surface to volume ratio. In these systems the biocatalyst (enzyme and/or microorganism) may be used either "free" or "immobilized".

Hollow fiber semi-permeable membranes are available in various pore sizes for any type of intended application. For the present method, the semi-permeable membrane has a molecular weight cutoff of from 10 to about 30 kDa which would allow only passage of small molecules (i.e., soluble oligosaccharides including small branched chain xylose oligomers), thus preventing the bulky enzymes sequestered within the confines of the hollow fiber circulation loop from leaking into the saccharification and fermentation vessels and isolating the pretreated biomass in the saccharification vessel from the hollow fiber circulation loop enzymes and the fermentation vessel.

The hollow fiber semi-permeable membrane used in the present method may be made of materials such as polysulfone (PSf), hydroxylated polysulfone (OHPSf), polyethersulfone (PES), hydroxylated polyether sulfone (OHPES), sulfonated polysulfone, polyetherketone (PEK), polyetheretherketone (PEEK), polyimide (PI), polyetherimide (PEI), or any combination thereof.

Application of Hollow Fiber Circulation Loop to Facilitate Saccharification and to Prevent Enzyme Inhibition In one embodiment the present method allows application of CSSF for saccharification of pretreated biomass and fermentation of resulting sugars to desirable target products in separate saccharification and fermentation vessels linked together via a hollow fiber circulation loop, containing two hollow fiber semi-permeable membranes. where at least one oligosaccharide hydrolyzing enzyme is sequestered.

The pretreated biomass is added along with a saccharification enzyme consortium to the saccharification vessel wherein the pretreated biomass is acted upon to produce high and low molecular weight components. Components of the saccharified biomass are delivered through a first circulation loop to a first hollow fiber semi-permeable membrane filter. The semi-permeable membrane prevents diffusion of the high molecular weight components of the pretreated biomass while allowing diffusion of the soluble low molecular weight components (less than 30 kDa). The molecular weight components pass through the semi-permeable membrane in to a hollow fiber circulation loop containing at least one sequestered saccharification enzyme.

The sequestered enzymes within the hollow fiber circulation loop act upon one or more diffused low molecular weight oligosaccharides in the hollow fiber circulation loop whereby at least one sugar product is formed. The product thus formed is then delivered through a second semi-permeable membrane filter into a second circulation loop and to the fermentation vessel wherein it is fermented to a target product by suitable microorganisms.

In an embodiment, the sequestered enzymes may include β-xylosidases, xylanase, β-glucosidase and arabinofuranosidases. The cellobiose, xylobiose and branched chain xylose oligomers of the saccharified biomass diffuse through the first hollow fiber semi-permeable membrane and enter the hollow fiber circulation loop where they are hydrolyzed to glucose, xylose and arabinose by β-glucosidase, β-xylobiosidase and the branched chain xylose oligomer hydrolyzing enzymes respectively. Any feedback inhibition of glucose, xylose and arabinose on the sequestered enzymes (e.g., β-glucosidase, β-xylosidase, xylanase and arabinofuranosidase) is relieved by passage of the products through the second semi-permeable membrane to the second circulation loop and into the fermentation vessel where they are consumed by a biocatalyst in fermentation. The sequestered enzymes are then recycled to act on more substrates from the saccharification vessel via the first external circulation loop. This system allows the cost-effective reuse of sequestered enzymes while relieving end-product feedback inhibition of enzymes in both the saccharification vessel and in the hollow fiber circulation loop. The sequestered enzymes may also be immobilized such that the contents of the hollow fiber circulation loop passes over a matrix containing the immobilized enzymes. Such immobilization may provide additional stabilization of the enzymes (e.g., to thermal denaturation). By using separate vessels, problems associated with the different temperature requirements of saccharification and fermentation are eliminated. Heat generated in the fermentation vessel or transported between the vessels may be delivered to the saccharification vessel by using a heat pump. The microorganism in the fermentation vessel is also not in direct contact with undigested biomass, eliminating possible losses of fermentation capacity through cell adsorption to biomass. Removal of the target product is also done in the absence of undigested or incompletely digested biomass.

Apparatus and Process for CSSF

In one embodiment CSSF occurs in an apparatus for processing pretreated biomass comprising: a saccharification vessel and a separate fermentation vessel wherein said vessels are connected by two external circulation loops and a hollow fiber circulation loop that connects the two external circulation loops and comprises semi-permeable membranes wherein said apparatus provides for compartmentalized simultaneous saccharification and fermentation of pretreated biomass.

Figure 2:
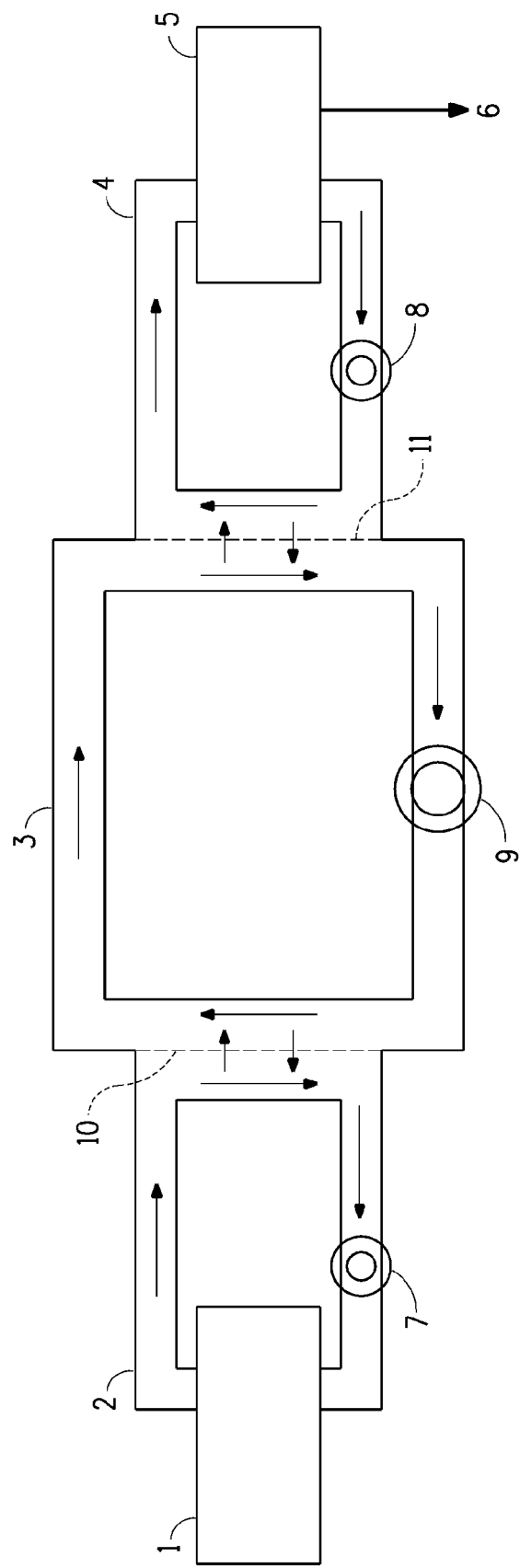
FIG. 2 is a schematic representation of a compartmentalized simultaneous saccharification and fermentation apparatus where separate saccharification and fermentation vessels are coupled by two external circulation loops and a hollow fiber circulation loop.

An embodiment of the present apparatus is shown in FIG. 2. This Figure depicts a block diagram of an apparatus for CSSF of pretreated biomass wherein separate vessels for saccharification and fermentation are connected via two external circulation loops and a hollow fiber circulation loop as follows. saccharification vessel (1); first external circulation loop (2); hollow fiber circulation loop (3); second external circulation loop (4); fermentation vessel (5); outlet for the target product (6); first circulation pump for the first external circulation loop (7); second circulation pump for the second external circulation loop (8); third circulation pump for the hollow fiber loop (9); the first semi-permeable membrane (10) of the hollow fiber circulation loop and second semi-permeable membrane (11) of the hollow fiber circulation loop (3).

In one embodiment a method of employing the apparatus of FIG. 2 is as follows. The saccharification vessel (1), which is typically maintained at temperatures from 35° C. to 55° C. and at a pH from 4 to about 6, contains partially saccharified biomass containing cellobiose, xylobiose, xylose oligomers and a saccharification enzyme consortium. A first external circulation loop (2) passes the biomass and the saccharification enzyme consortium from the saccharification vessel over the outside of a first hollow fiber semi-permeable membrane (10), the inside of which is part of the hollow fiber circulation loop (3). The polysaccharides of the biomass and the enzymes of the saccharification consortium, due to their large molecular size, are excluded from passing through the hollow fiber semi-permeable membrane into the hollow fiber circulation loop while smaller molecules such as cellobiose, xylobiose and branched chain xylose oligomers can pass through the membrane. The β-glucosidase, β-xylosidase, xylanase and branched chain xylose oligomer hydrolyzing enzymes are sequestered within the hollow fiber circulation loop. The β-glucosidase acts on the small soluble substrate (cellobiose) which can pass through the first semi-permeable membrane (10). β-Xylobiosidase, a β-xylosidase type enzyme, converts xylobiose, which can also pass through the first semi-permeable membrane, to xylose. The branched chain xylose oligomer hydrolyzing enzymes convert the branched chain xylose oligomers (e.g., L-arabinose linked to a xylose oligomeric backbone through an α-1,2 linkage), which can pass through the first semi-permeable membrane, to be hydrolyzed to xylose and arabinose. The glucose, xylose and arabinose thus generated in the hollow fiber circulation loop, are delivered, via the second semi-permeable membrane, (11) and the second external circulation loop (4), to the fermentation vessel (5) wherein they are converted to target product(s) by microorganisms. The second pump (9) in the hollow fiber loop continuously recirculates the sequestered enzymes and allows for their repeated use in their respective reactions. The enzymes' repeated use and the overall lower quantity of enzyme required for the process, results in a significant overall cost savings. Additionally, the disclosed method is a unique CSSF process which obviates the need for the lignocellulosic substrate and the fermenting microorganism to be in the same vessel, thus, overcoming challenges such as temperature incompatibility. Removal of the target product in the fermentation vessel (6) helps to drive the whole process to completion. The first and third external loop pumps (7) and (8) allow recirculation of various components among the saccharification and fermentation vessels and the hollow fiber circulation loop.

In this method, since the microorganism is not in direct contact with undigested biomass, possible losses of fermentation capacity through cell adsorption to biomass is eliminated.

Also removal of target product from the fermentation vessel such as by distillation, permselective membranes, pervaporation or other suitable methods is not hampered by the presence of undigested biomass.

Saccharification and fermentation vessels are well-known in the art and one of ordinary skill in the art is familiar with their application.

Fermentation to Target Products

Various fermentation methods, with suitable microorganisms, may be used for conversion of the fermentable sugars released from pretreated saccharified biomass to produce target products. For the present method either a fed-batch or continuous fermentation system may be employed. These methods are well-known in the art and one of ordinary skill in the art is familiar with their application. "Fed-Batch" fermentation processes comprise a typical batch system with the exception that substrate is added as the fermentation progresses. Batch and Fed-Batch fermentations are common and well known in the art and examples may be found in Thomas D. Brock in *Biotechnology: A Textbook of Industrial Microbiology*, Second Edition (1989) Sinauer Associates, Inc., Sunderland, Mass., or Deshpande, Mukund V., Appl. Biochem. Biotechnol., 36:227, (1992), herein incorporated by reference. The current method is anticipated to be adaptable to "continuous" fermentation methods as well. Continuous fermentation is an open system where fermentation medium is added continuously to a bioreactor and an equal amount of conditioned medium is removed simultaneously for processing.

Various types of growth media may be used in the present invention. Such growth media may be supplemented with, for example, yeast extract, specific amino acids, phosphate, nitrogen sources, salts, and trace elements. Components required for production of a specific product made by a specific biocatalyst may also be included, such as an antibiotic to maintain a plasmid or a cofactor required in an enzyme catalyzed reaction. Also additional sugars may be included to increase the total sugar concentration.

Temperature and/or headspace gas may also be adjusted, depending on conditions useful for the fermentation microorganism(s). Fermentation may be aerobic or anaerobic. According to the method described herein, fermentation of one or more sugars and saccharification occur simultaneously, but in separate compartments, and is defined as compartmentalized simultaneous saccharification and fermentation (CSSF).

The fermentation of sugars to target products may be performed by one or more appropriate microorganisms such as bacteria, filamentous fungi and yeast. Both wild type and recombinant microorganisms could be used. Such microorganisms include, but are not limited to, *Escherichia, Zymomonas, Saccharomyces, Candida, Pichia, Streptomyces, Bacillus, Lactobacillus,* and *Clostridium.*

Target products include, without limitation, alcohols (e.g., arabinitol, butanol, ethanol, glycerol, methanol, 1,3-propanediol, sorbitol, and xylitol); organic acids (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, propionic acid, succinic acid, and xylonic acid); ketones (e.g., acetone); amino acids (e.g., aspartic acid, glutamic acid, glycine, lysine, serine, and threonine); gases (e.g., methane, hydrogen ($H_2$), carbon dioxide ($CO_2$), and carbon monoxide (CO)).

Fermentation processes also include processes used in the consumable alcohol industry (e.g., beer and wine), dairy industry (e.g., fermented dairy products), leather industry, and tobacco industry.

Further to the above, additional general products such as: organic products, chemicals, fuels, commodity and specialty chemicals such as xylose, acetone, acetate, glycine, lysine, organic acids (e.g., lactic acid), 1,3-propanediol, butanediol, glycerol, ethylene glycol, furfural, polyhydroxyalkanoates, cis,cis-muconic acid, and animal feed (Lynd, L. R., Wyman, C. E., and Gerngross, T. U., Biocommodity engineering, Biotechnol. Prog., 15: 777-793, 1999; and Philippidis, G. P., Cellulose bioconversion technology, in Handbook on Bioethanol: Production and Utilization, Wyman, C. E., ed., Taylor & Francis, Washington, D.C., 179-212, 1996; and Ryu, D. D. Y., and Mandels, M., Cellulases: biosynthesis and applications, Enz. Microb. Technol., 2: 91-102, 1980) may be produced using the instant method.

Potential co-products may also be produced, such as multiple organic products from fermentable carbohydrate. Lignin-rich residues remaining after saccharification and fermentation can be converted to lignin-derived chemicals, chemical building blocks or used for power production.

Target products may be produced following passage of certain components of the pretreated saccharified biomass through the hollow fiber-containing circulation loop to the fermentation vessel as described herein.

Target products may be removed from the fermentation vessel by such methods as distillation, using permselective membranes, or pervaporation or non-selectively by batch-wise or continuous replenishment of the fermentation broth. Target product removal helps to drive the overall reaction to completion.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

Materials

Saccharification enzymes were obtained from the following sources. Spezyme® CP and Multifect® Xylanase (Genencor International, Palo Alto, Calif.) and Novozyme 188 (Novozymes, 2880 Bagsvaerd, Denmark).

Sugar cane bagasse, which was milled in a Wiley knife mill through a 1 mm sieve, was used herein.

Abbreviations Used in the Examples

The following abbreviations are used in the Examples: "° C." is degrees Centigrade or Celsius; "%" is percent; "mL" is milliliter; "h" is hour(s); "rpm" is revolution per minute; "EtOH" is ethanol; "mg/mL" is milligram per mililiter; "g/100 mL" is gram per 100 milliliters; "N" is normal; "g" is gram; "NaOH" is sodium hydroxide; "v/v" is volume for volume; "mm" is millimeter; "mL/min" is milliliter per minute; and "min" is minute(s), "mM" is millimolar, "mg protein/g cellulose" means milligram protein per gram cellulose, "kDa" means kiloDalton.

Example 1

Increasing the β-Glucosidase Concentration Decreases the Requirement for Cellulase by Decreasing End-Product Inhibition During Biomass Scarification To prepare biomass for saccharification, it was first pretreated as described herein. Knife-milled sugar cane bagasse (2 g) was suspended in 15 mL of 100 mM $H_2SO_4$ and the suspension was autoclaved in sealed glass vials for 1 hour at 121° C. The contents were cooled and placed in two disposable chromatographic column cartridges containing fritted plastic filters, placed in 15 mL conical tubes and centrifuged at room temperature at 3000 rpm using a HS-4 swinging bucket rotor in a RC-5B Sorvall centrifuge (Thermo Fisher Scientific, Waltham, Mass.) to wash the pretreated biomass. Each column was washed 3 times with 5 mL $H_2O$ before each was washed twice with 2.5 mL 69% (v/v) EtOH in $H_2O$ plus NaOH (5 mg/1.75 mL) and anthraquinone (1 mg/1.75 mL). The wet pretreated biomass residue, which weighed 3.8 g (1.4 g dry matter), was suspended in an additional 4.6 g of wash solution. The suspension was placed in a stainless steel pressure vessel (19 mL internal volume), capped and heated at 175° C. for 140 min. The pressure vessel was cooled to room temperature and the contents centrifuged in 2 chromatographic column cartridges as described above. The pretreated biomass in each column was washed 4 times with 1.5 mL of 69% (v/v) EtOH in $H_2O$. The pretreated biomass residue was then air-dried (~92% dry biomass).

The air-dried pretreated biomass sample (78.7% glucan, 5.5% xylan) was suspended in 50 mM NaCitrate buffer, pH 4.6 at a solids loading of ~11%. Spezyme® CP cellulase, Multifect® Xylanase, and Novozyme 188 were added at different ratios and concentrations per g cellulose. These ratios (mg protein/g cellulose) were: 4:3:8, 8:3:4, 6:3:6, 6:6:12, 12:6:1.2 and 12:6:12. In addition, 1% Tween 20 (w/v) and 0.01% (w/v) $NaN_3$ were added. Sample volumes of ~0.5 mL were added to 6 mL screw cap vials containing two glass beads (3 mm) and were incubated at 46° C. on a rotary shaker (250 rpm). Aliquots were removed at 4 h and at every 24 h after the start of incubation and diluted 41.25-fold with 0.01 N $H_2SO_4$ for analysis. Samples were filtered through Spin-X filters (Corning. Inc., Corning, N.Y.) and the filtrates analyzed by HPLC (Agilent series 1100/1200, Agilent, Palo Alto, Calif.). A BioRad HPX-87H Aminex column (BioRad, Hercules, Calif.) was used to fractionate the released sugars using 0.01 N $H_2SO_4$ as the mobile phase. The column was maintained at 60° C. and the flow rate at 0.6 mL/min. A refractive index detector, maintained at 55° C., was used to detect the eluted sugars.

Figure 1B:
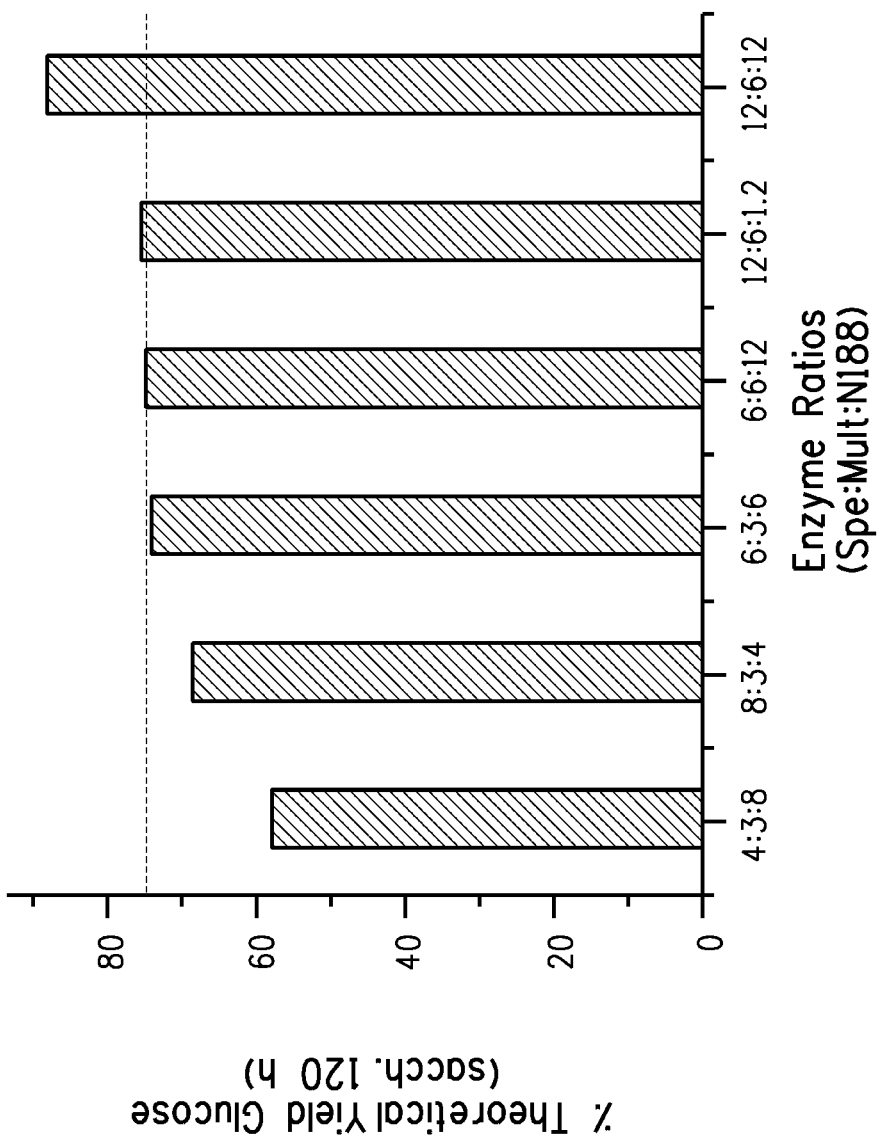

FIG. 1A shows the time course of saccharification of the biomass at different enzyme loadings with yields of monomeric glucose expressed as percent theoretical yield only for saccharification. FIG. 1B shows a comparison of monomeric glucose yields at 120 h from FIG. 1A for the different enzyme ratios. The enzymatic saccharification experiments using Spezyme® CP:Multifect® Xylanase:Novozyme 188 loadings of [6:3:6], [6:6:12] and [12:6:1.2] per g cellulose gave virtually the same yields at 120 h incubation. The results show that lowering of the Spezyme® CP enzyme loading may be compensated for by increased loading of Novozyme 188 (mostly β-glucosidase). Based on these results, if the β-glucosidase were stable and reusable, then its reusability and its ability to replace some of the cellulase may result in a reduced cost of cellulase enzyme per amount of monomeric sugar produced.

Example 2

Prophetic

A Double Hollow Fiber Circulation Loop Entraps the β-Glucosidase and the β-Xylobiosidase Enzymes to Relieve End-Product Inhibition and Allow their Recycle Based on the results disclosed in Example 1, a process in which the biomass saccharification products are removed and wherein the β-glucosidase and β-xylobiosidase enzymes are recycled, may provide significant cost savings for production of fermentable sugars.

A schematic representation of a continuous SSF apparatus that uses separate vessels for saccharification and fermentation which are linked by a semi-permeable hollow fiber circulation loop is shown in FIG. 2. The saccharification vessel (1) is maintained at 46° C. and pH 5. Pretreated biomass is added to the saccharification vessel together with cellulase and xylanase. Small hexose and pentose oligomers including cellobiose and xylobiose that are produced by the enzymatic saccharification reactions are transferred via the first external circulation loop (2) to the first semi-permeable hollow fiber membrane (10) where they pass through the membrane into the hollow fiber circulation loop (3). The hollow fiber circulation loop contains sequestered β-glucosidase and β-xylobiosidase enzymes. These enzymes are large molecules that cannot diffuse through the hollow fiber membrane which has a molecular weight cutoff of 30 kDa. However, the semi-permeable membrane is permeable to small molecule reactants (cellobiose and xylobiose) and products (glucose and xylose) of these reactants. The β-glucosidase and β-xylobiosidase enzymes hydrolyze cellobiose and xylobiose to glucose and xylose. The glucose and xylose thus formed are transferred to the second semi-permeable membrane (11), and through the membrane into the second external circulation loop (4) and the fermentation vessel (5). The fermentation vessel, which may be maintained at 30-33° C. and pH 5.8, contains the required growth medium and suitable microorganism(s) for production of a target product, for example ethanol or butanol. During the fermentation, the target product may be removed form the fermentation vessel via outlet (6). Removal of the product from the fermentation vessel (e.g. by sparging or via a permselective membrane, or pervaporation) assists in driving the reaction towards completion. Circulation loop (2) returns the biomass that is partially depleted of cellobiose and xylobiose to the saccharification vessel. First and third circulation pumps (7) and (8) circulate the contents of the first and second external loops, respectively. Second circulation pump (9) circulates the contents of the internal hollow fiber circulation loop (including the β-glucosidase and β-xylobiosidase enzymes) for an additional round of reaction. Thus, the end product inhibition of the exocellulase and xylanase in the saccharification vessel is relieved by the β-glucosidase and β-xylobiosidase enzymes contained within the internal hollow fiber loop, driving the overall reaction to completion, affording a more economical process for conversion of biomass to the target product.

What is claimed is:

1. An apparatus for processing pretreated biomass consisting of: a saccharification vessel that is connected to a first external circulation loop wherein said first external circulation loop is external to and connected to a first semi-permeable membrane of a hollow fiber circulation loop comprising a sequestered saccharification enzyme; and wherein said hollow fiber circulation loop is connected to a second external circulation loop that is external to and connected to a second semi-permeable membrane of the hollow fiber circulation loop; and wherein said second external circulation loop is connected to a fermentation vessel with an outlet for a target product;

wherein the first external circulation loop carries biomass and enzyme from the saccharification vessel over the outside of the first semi-permeable membrane of the hollow fiber circulation loop; and wherein the reaction products of the hydrolyzed which pass through the first semi-permeable membrane are delivered to the hollow fiber circulation loop and then in turn to the fermentation vessel containing fermentation media and at least one biocatalyst via the second circulation loop and by passing through the second semi-permeable membrane; and wherein the second external circulation loop recirculates the fermentation medium and biocatalyst to the first external circulation loop via the first semi-permeable membrane.

2. The apparatus of claim 1, further comprising a series of circulation pumps including a first circulation pump for the first external circulation loop; a second circulation pump for the second external circulation loop; a third circulation pump for the internal hollow fiber loop.

3. The apparatus of claim 1 wherein the semi-permeable membranes are made of a material selected from the group consisting of: polysulfone, hydroxylated polysulfone, polyethersulfone, hydroxylated polyethersulfone, sulfonated polysulfone, polyetherketone, polyetheretherketone, polyimide, and polyetherimide.

4. The apparatus of claim 1 wherein the semi-permeable membranes have molecular weight permeability of from about 10 to about 30 kiloDaltons.

5. A method of processing pretreated biomass comprising:
(a) providing the apparatus of claim 2,
(b) providing a mixture of pretreated biomass and a saccharification enzyme consortium to the saccharification vessel of said apparatus wherein said mixture produces both high and low molecular weight components by saccharification;
(c) providing at least one sequestered enzyme in the hollow fiber circulation loop;
(d) delivering an amount of the mixture of (b) through the first circulation loop over the first hollow fiber semi-permeable membrane whereby said high molecular weight components of the mixture of (b) do not diffuse through said membrane and said low molecular weight components of the mixture diffuse through said membrane into the hollow fiber circulation loop;
(e) hydrolyzing the low molecular weight components that diffuse into the hollow fiber circulation loop in (d) by said at least one sequestered enzyme in said hollow fiber circulation loop whereby hydrolysate comprising fermentable sugars is formed; and (f) delivering hydrolysate comprising fermentable sugars through a second semi-permeable membrane into a second circulation loop and to a fermentation vessel;

wherein pretreated biomass components are circulated throughout the apparatus by circulation pumps, and wherein pretreated biomass is processed.

6. The method of claim 5, wherein said saccharification enzyme consortium of (b) comprises enzymes selected from the group consisting of: cellulases, xylanases, glycosidases, ligninases and esterases.

7. The method of claim 5 wherein the sequestered enzyme of (c) comprises an enzyme selected from the group consisting of: β-glucosidase β-xylosidase and xylanases that can hydrolyze soluble branched chain xylose oligomers.

8. The method of claim 5 wherein the fermentable sugars of (e) delivered to the fermentation vessel in (f) are converted by at least one microorganism to at least one target product.

9. The method of claim 8 wherein the target product is selectively removed from the fermentation vessel.

10. The method of claim 5 wherein hydrolysate formed by the action of said sequestered enzyme on biomass is delivered to said fermentation vessel.

11. The method of claim 5 wherein said sequestered enzyme of (c) is recycled multiple times.

12. The method of claim 5 wherein said first and said second semi-permeable membrane are each made of a material selected from the group consisting of: polysulfone, hydroxylated polysulfone, polyethersulfone, hydroxylated polyether sulfone, sulfonated polysulfone, polyetherketone, polyetheretherketone, polyimide, and polyetherimide.

* * * * *